US008236282B2

(12) United States Patent
Klunk et al.

(10) Patent No.: US 8,236,282 B2
(45) Date of Patent: Aug. 7, 2012

(54) BENZOTHIAZOLE DERIVATIVE COMPOUNDS, COMPOSITIONS AND USES

(75) Inventors: William E. Klunk, Pittsburgh, PA (US); Chester A. Mathis, Jr., Pittsburgh, PA (US); Yanming Wang, Imperial, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 273 days.

(21) Appl. No.: 12/570,379

(22) Filed: Sep. 30, 2009

(65) Prior Publication Data

US 2010/0021388 A1 Jan. 28, 2010

Related U.S. Application Data

(63) Continuation of application No. 10/645,847, filed on Aug. 22, 2003, now abandoned.

(51) Int. Cl.
*A61K 51/00* (2006.01)
*A61M 36/14* (2006.01)
(52) U.S. Cl. ............ 424/1.89; 424/1.11; 424/1.65; 424/1.81; 424/1.85
(58) Field of Classification Search .......... 424/1.11, 424/1.65, 1.81, 1.85, 1.89, 9.1, 9.2, 9.3, 9.4, 424/9.5, 9.6; 548/146
See application file for complete search history.

(56) References Cited

U.S. PATENT DOCUMENTS

| | | | |
|---|---|---|---|
| 3,257,204 A | 6/1966 | Sus et al. | |
| 4,500,340 A | 2/1985 | Becker et al. | |
| 4,540,648 A | 9/1985 | Scheler | |
| 5,935,927 A | 8/1999 | Vitek et al. | |
| 6,417,178 B1 | 7/2002 | Klunk et al. | |
| 7,270,800 B2 | 9/2007 | Klunk et al. | |
| 7,351,401 B2 | 4/2008 | Klunk et al. | |
| 2003/0236391 A1 | 12/2003 | Klunk et al. | |
| 2006/0083677 A1 | 4/2006 | Brady et al. | |

FOREIGN PATENT DOCUMENTS

| | | | |
|---|---|---|---|
| CA | 2 382 406 A1 | | 3/2001 |
| EP | 0 081 141 B1 | | 12/1981 |
| EP | 0 287 909 B1 | | 10/1988 |
| EP | 0 118 086 B1 | | 9/1989 |
| JP | 59-165050 | | 9/1984 |
| JP | 09-501944 | | 2/1997 |
| JP | 2006-510705 | | 3/2006 |
| WO | WO 95/06469 | | 3/1995 |
| WO | WO 97/26919 | | 7/1997 |
| WO | WO-98/17267 | | 4/1998 |
| WO | WO-01/14354 | * | 3/2001 |
| WO | WO 01/14354 A1 | | 3/2001 |
| WO | WO 02/16333 A2 | | 2/2002 |
| WO | WO 02/051821 A1 | | 7/2002 |
| WO | WO 02/085903 A2 | | 10/2002 |
| WO | WO 2004.056399 A2 | | 7/2004 |
| WO | WO 2004/056399 A2 | | 7/2004 |

OTHER PUBLICATIONS

Wang et al (J. Mol. Neurosci., 2002, vol. 19, Nos. 1-2, pp. 11-16).*
Bogert et al., "Researches on Thiazoles, XVII. An Investigation of the Connection Between Constitution and Color in the Thioflavine Group", Collection of Czechoslovak Chemical Communications, 1931, pp. 480-498, vol. 3, The Chemical Laboratories.
Chester A. Mathis et al., "Synthesis and Evaluation of 11C-Labeled 6-Substituted 2-Arylbenzothiazoles as Amyloid Imaging Agents", J. Med. Chem., 2003, 46, pp. 2740-2754.
Cuadro et al., "Styryl and Azastyryl 1,3-Benzazoles with Antihelmitic Activity", II Farmaco, 1992, pp. 477-488, vol. 47, No. 4.
Dryanska, "(-Hydroxybenzylation and Benzylidenation of the Methyl Group in 2-Methyl-1,3-benzoxazole and 2-Methyl-1,3-benzothiazole" Communications, 1976, pp. 37-38.
Final Office Action U.S. Appl. No. 11/828,554 dated Aug. 6, 2009.
Fokken et al., "Beitrag zur Darstellung von Verbindungen mit Amidino-bzw. Amidoximstruktur", Pharmazie, 1977, pp. 566-569, Pharmazie 32, H.10 (19).
Grozinger et al., Heterocyclic ethenyloxanilates as orally active antiallergic agents, Eur. J. Med. Chem. Chim. Ther., 1985, pp. 487-491, vol. 20, No. 6.
Klunk et al., "Uncharged thioflavin-T derivatives bind to amyloid-beta protein with high affinity and readily enter the brain", Life Sciences, 2001, pp. 1471-1484, vol. 69, No. 13, Elsevier Pub.
Martvon et al., "2-Phenyl-6-Benzothiazolyl Isothiocyanates", Collection Czechoslov, Chem. Commun. 1974, pp. 1356-1365, vol. 39, No. 5.
Mathis et al., "Lipophilic 11C-labelled thioflavin-T analogues for imaging amyloid plaques in Alzheimer's disease", Journal of Labelled Compounds and Radiopharmaceuticals, 2001, pp. S26-S28, vol. 44, No. Supp. 1.
Non Final Office Action dated Mar. 13, 2009 for U.S. Appl. No. 12/046,070.
Non-Final Office Action U.S. Appl. No. 11/828,554 dated Dec. 5, 2008.
Non-Final Office Action U.S. Appl. No. 12/046,070 dated Mar. 13, 2009.
Notice of Allowance U.S. Appl. No. 11/828,554 dated Aug. 13, 2010.
Notice of Reasons for Rejection Japanese Patent Application No. 2002-521434 dated Sep. 7, 2011.
Shi et al., "Antitumor Benzothiazoles, 3.1 Synthesis of 2-(4-Aminophenyl)benzothiazoles and Evaluation of Their Activities against Breast Cancer Cell Lines in Vitro and in Vivo", J. Med. Chem., 1996, pp. 3375-3384, vol. 39, The American Chemical Society.
U.S. Appl. No. 12/046,070 Final Office Action Dated Sep. 9, 2009.
Vaz et al., "6-Substituted 2-(p-aminostyryl)benzothiazole derivatives", Indian J. Chem., 1976, Sect. B, pp. 709-711, vol. 14B, No. 9.

(Continued)

*Primary Examiner* — D L Jones
(74) *Attorney, Agent, or Firm* — Stephen A. Bent; Foley & Lardner LLP

(57) ABSTRACT

This invention provides benzothiazole derivative compounds, compositions comprising such compounds, methods of preparing such compounds, and methods of using such compounds for detecting amyloid deposit(s) and for diagnosing a disease, disorder or condition characterized by amyloid deposit(s).

4 Claims, 4 Drawing Sheets

OTHER PUBLICATIONS

Zhuang et al., "Radioiodianted Styrylbenzenes and Thioflavins as Probes for Amyloid Aggregates", Journal of Medicinal Chemistry, vol. 44, No. 12, 2001, pp. 1905-1914.

Examiner's Answer U.S. Appl. No. 10/645,847 dated Sep. 3, 2008.

Advisory Action U.S. Appl. No. 10/654,847 dated May 6, 2008.

Final Office Action U.S. Appl. No. 10/654,847 dated Oct. 18, 2007.

Non-Final Office Action U.S. Appl. No. 10/645,847 dated May 2, 2007.

Wang et al. (Journal of Molecular Neuroscience) 2002, vol. 19, Nos. 1-2, pp. 11-16.

Final Office Action U.S. Appl. No. 10/645,847 dated Aug. 11, 2006.

Dwight L. Deardorff PhD, "Isotonic Solutions freezing-point calculations tonicity testing methods", Remingtons Pharmaceutical Sciences, 15th Ed. Easton: Mack Publishing Co., pp. 1405-1412.

Kenneth E. Avis DSc, "Parenteral Preparations history administration components production quality control packaging labeling", Remingtons Pharmaceutical Sciences, 15th Ed. Easton: Mack Publishing Co., pp. 1461-1487.

"The Significance of Drug Metabolism in Medicinal Chemistry", Burger's Medicinal Chemistry and Drug Chemistry, Fifth Ed. vol. 1, pp. 172-178 (1995).

C.A. Mathis et al., "Development of $^{18}$F-Labelled Thioflavin-T Analogues as Amyloid Plaque Imaging Agents", J. Label Compd. Radiopharm. 2003: 46: S62.

L.A. Balant et al., "Metabolic Considerations in Prodrug Design", Burger's Medicinal Chemistry and Drug Discovery, Fifth Edition, vol. 1, Chapter 23, pp. 949-982.

Canadian Office Action dated Oct. 7, 2009 for Application No. 2 419 420.

Canadian Office Action dated Nov. 27, 2009 for Application No. 2 438 032.

Klunk et al., (Life Sciences, Aug. 17, 2001, vol. 69, No. 13, pp. 1471-1484).

Mathis et al., (J. Med. Chem., May 24, 2003, vol. 46, No. 13, pp. 2740-2754).

Non-Final Office Action U.S. Appl. No. 10/645,847 dated Jan. 26, 2006.

Translation Japanese Office Action Patent Application No. 2006-507179 dated Jul. 13, 2010.

Yanming Wang et al., "Synthesis and Evaluation of 2-(3'-Iodo-4'-aminophenyl)-6-hydroxybenzothiazole for In Vivo Quantitation of Amyloid Deposits in Alzheimer's Disease", Journal of Molecular Neuroscience, vol. 19, 2002, pp. 11-16.

Chester A. Mathis et al., "A Lipophilic Thioflavin-T Derivative for Positron Emission Tomography (PET) Imaging of Amyloid in Brain" Bioorganic & Medicinal Chemistry Letters 12 (2002) 295-298.

Suo-Qin Zhang et al., "A ZINDO-SOS Study on Nonlinear Second-order Optical Properties of 2-Phenylbenzothiazole and It's Derivatives", Chemical Journal of Chinese Universities, Vol. 23, No. 9, 1772-1775, 2002.

Notice of Reasons for Rejection Japanese Patent Application No. 2006-507179 dated Jul. 13, 2010.

Chester A. Mathis et al., "A Lipophilic Thioflavin-T Derivative for Positron Emission Tomography (PET) Imaging of Amyloid in Brain", Bioorganic & Medicinal Chemistry Letters, 12 (2002) 295-298.

Chemical Journal of Chinese Universities, 2002, vol. 23, No. 9, pp. 1772-1775.

Zh. Obshch. Khim., 1950, vol. 20, pp. 1807-1815.

* cited by examiner

US 8,236,282 B2

BENZOTHIAZOLE DERIVATIVE COMPOUNDS, COMPOSITIONS AND USES

CROSS-REFERENCE TO RELATED PATENT APPLICATIONS

This application is a Continuation Application of U.S. Ser. No. 10/645,847 filed Aug. 22, 2003, which is incorporated herein by reference in its entirety.

BACKGROUND OF THE INVENTION

Studies suggest that amyloid deposition in the brain is an early, causative event in the pathogenesis of Alzheimer's disease (AD). Progression of amyloid deposition results in the formation of neuritic plaques and neurofibrillary tangles in regions of the brain that are involved with learning and memory. A typical Alzheimer's neuritic plaque comprises dystrophic neurites surrounding a core of amyloid material. The principal component of the amyloid core is a protein called amyloid-beta (Aβ).

Since the initial deposition of amyloid may occur long before clinical symptoms of AD are noticeable, the detection and quantitation of amyloid deposits could facilitate the diagnosis of AD in its early, pre-symptomatic stages. See U.S. Pat. No. 6,417,178 and U.S. Publication No. 2002033019. Imaging techniques, such as positron emission tomography (PET) and single photon emission computed tomography (SPECT), are effective in monitoring the accumulation of amyloid deposits in the brain and correlating it to the progression of AD. The application of these techniques requires the development of radioligands that readily enter the brain and selectively bind to amyloid deposits in vivo.

Thus, a need exists for radiolabeled amyloid binding compounds that are non-toxic, bioavailable and capable of crossing the blood-brain barrier.

SUMMARY OF THE INVENTION

This invention provides benzothiazole derivative compounds, compositions comprising such compounds, methods of preparing such compounds, and methods of using such compounds for detecting amyloid deposit(s) and for diagnosing a disease, disorder or condition characterized by amyloid deposit(s).

DETAILED DESCRIPTION

Definitions

Figure 1:
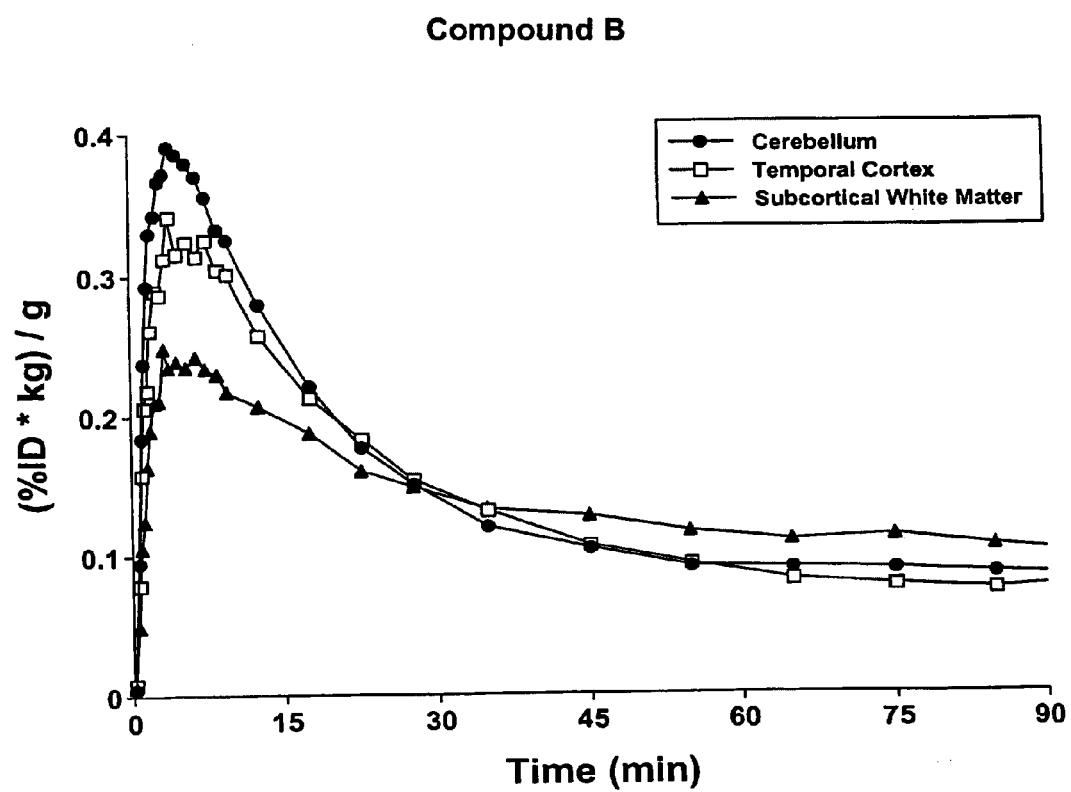
FIG. 1 shows time-activity curves of the penetration and clearance of radioactivity from three regions of baboon brain following the injection of Compound B (2-(3-[$^{18}$F]-fluoro-4-methylamino-phenyl)-benzothiazol-6-ol).

"Alkyl" refers to a saturated straight or branched chain hydrocarbon radical. Examples include without limitation methyl, ethyl, propyl, iso-propyl, butyl, iso-butyl, tert-butyl, n-pentyl and n-hexyl.

"Alkenyl" refers to an unsaturated straight or branched chain hydrocarbon radical comprising at least one carbon to carbon double bond. Examples include without limitation ethenyl, propenyl, iso-propenyl, butenyl, iso-butenyl, tert-butenyl, n-pentenyl and n-hexenyl.

"Alkynyl" refers to an unsaturated straight or branched chain hydrocarbon radical comprising at least one carbon to carbon triple bond. Examples include without limitation ethynyl, propynyl, iso-propynyl, butynyl, iso-butynyl, tert-butynyl, pentynyl and hexynyl.

"Alkoxy" refers to an alkyl group bonded through an oxygen linkage.

"Halo" refers to a fluoro, chloro, bromo or iodo radical.

"Radioactive halo" refers to a radioactive halo, i.e. radiofluoro, radiochloro, radiobromo or radioiodo.

"Effective amount" refers to the amount required to produce a desired effect. Examples of an "effective amount" include amounts that enable imaging of amyloid deposit(s) in vivo, that yield acceptable toxicity and bioavailability levels for pharmaceutical use, and/or prevent cell degeneration and toxicity associated with fibril formation.

"Pharmaceutically acceptable carrier" refers to a pharmaceutically acceptable material, composition or vehicle, such as a liquid or solid filler, diluent, excipient or solvent encapsulating material, involved in carrying or transporting the subject compound from one organ, or portion of the body, to another organ or portion of the body. Each carrier is "acceptable" in the sense of being compatible with the other ingredients of the formulation and suitable for use with the patient. Examples of materials that can serve as a pharmaceutically acceptable carrier include without limitation: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations as identified in REMINGTON'S PHARMACEUTICAL SCIENCES, 15th Ed. Easton: Mack Publishing Co. pp. 1405-1412 and 1461-1487 (1975), and THE NATIONAL FORMULARY XIV., 14th Ed. Washington: American Pharmaceutical Association (1975).

"Pharmaceutically acceptable salt" refers to an acid or base salt of the inventive compound, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Prodrug" refers to a derivative of the inventive compound that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compound using conventional methods, such as that described in BURGER'S MEDICINAL CHEMISTRY AND DRUG CHEMISTRY, Fifth Ed., Vol. 1, pp. 172-178, 949-982 (1995).

"Animal" refers to a living organism having sensation and the power of voluntary movement, and which requires for its existence oxygen and organic food. Examples include, without limitation, members of the human, equine, porcine, bovine, murine, canine and feline species. In the case of a human, an "animal" may also be referred to as a "patient."

"Mammal" refers to a warm-blooded vertebrate animal.

"Treating" refers to:

(i) preventing a disease, disorder or condition from occurring in an animal that may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

Compounds

This invention provides radiolabeled benzothiazole derivative compounds as amyloid imaging agents.

Specifically, this invention provides a compound of formula I

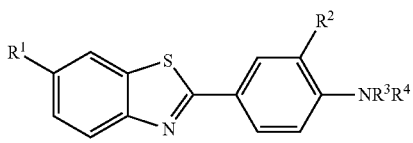

or a pharmaceutically acceptable salt, hydrate, solvate or prodrug of the compound, wherein:

$R^1$ is hydrogen, —OH, —$NO_2$, —CN, —COOR, —$OCH_2OR$, $C_1$-$C_6$ alkyl, $C_2$-$C_6$ alkenyl, $C_2$-$C_6$ alkynyl, $C_1$-$C_6$ alkoxy or halo;

$R^2$ is $C_1$-$C_6$ alkyl;

$R^2$ is hydrogen, a non-radioactive halo or a radioactive halo;

$R^3$ is hydrogen, $C_1$-$C_6$ alkyl, $C_2$-$C_6$ alkenyl or $C_2$-$C_6$ alkynyl; and $R^4$ is hydrogen, $C_1$-$C_6$ alkyl, $C_2$-$C_6$ alkenyl or $C_2$-$C_6$ alkynyl, wherein the alkyl, alkenyl or alkynyl comprises a radioactive carbon or is substituted with a radioactive halo when $R^2$ is hydrogen or a non-radioactive halo;

provided that when $R^1$ is hydrogen or —OH, $R^2$ is hydrogen and $R^4$ is —$^{11}CH_3$, then $R^3$ is $C_2$-$C_6$ alkyl, $C_2$-$C_6$ alkenyl or $C_2$-$C_6$ alkynyl; and further provided that when $R^1$ is hydrogen, $R^2$ hydrogen and $R^4$ is —$(CH_2)_3^{18}F$, then $R^3$ is $C_2$-$C_6$ alkyl, $C_2$-$C_6$ alkenyl or $C_2$-$C_6$ alkynyl.

Examples of a radioactive carbon include, without limitation, $^{11}C$, $^{13}C$ and $^{14}C$. Examples of a radioactive halo include, without limitation, $^{131}I$, $^{121}I$, $^{124}I$, $^{123}I$, $^{76}Br$, $^{75}Br$, $^{18}F$. In one embodiment, the radioactive halo is $^{125}I$, $^{124}I$, $^{123}I$ or $^{18}F$. In another embodiment, $R^1$ is —OH.

In yet one embodiment, $R^1$ is hydrogen, —OH, —CN, $C_1$-$C_6$ alkyl, $C_2$-$C_6$ alkenyl, $C_2$-$C_6$ alkynyl, $C_1$-$C_6$ alkoxy or halo; $R^2$ is hydrogen; and $R^4$ is $C_1$-$C_6$ alkyl, $C_2$-$C_6$ alkenyl or $C_2$-$C_6$ alkynyl, wherein the alkyl, alkenyl or alkynyl comprises a radioactive carbon. As an example of this embodiment, $R^1$ is hydrogen, —OH, —CN, —$OCH_3$, —$CH_3$ or —Br; $R^3$ is hydrogen or —$CH_3$; and $R^4$ is —$^{11}CH_3$.

In yet another embodiment, $R^2$ is a non-radioactive halo or a radioactive halo, wherein the halo is iodo; and $R^4$ is hydrogen, $C_1$-$C_6$ alkyl, $C_2$-$C_6$ alkenyl or $C_2$-$C_6$ alkynyl, wherein the alkyl, alkenyl or alkynyl comprises a radioactive carbon when $R^2$ is a non-radioactive halo. As an example of this embodiment, R is —$CH_3$; and the radioactive carbon in $R^4$ is $^{11}C$. As another example, $R^1$ is —OH or $C_1$-$C_6$ alkoxy; $R^2$ is a radioiodine; and $R^3$ and $R^4$ are independently hydrogen or $C_1$-$C_6$ alkyl. As a further example, $R^1$ is —OH; $R^2$ is —$^{123}I$ or —$^{125}I$; and $R^3$ and $R^4$ are each hydrogen.

In yet another embodiment, $R^2$ is hydrogen, radiobromo, radiochloro or radiofluoro.

In yet another embodiment, $R^2$ is a radiofluoro. As an example of this embodiment, $R^1$ is —OH or $C_1$-$C_6$ alkoxy; $R^2$ is $^{18}F$; and $R^3$ and $R^4$ are independently hydrogen or $C_1$-$C_6$ alkyl. As another example, $R^2$ is —OH; $R^3$ is hydrogen; and $R^4$ is —$CH_3$.

In yet another embodiment, $R^4$ is $C_1$-$C_6$ alkyl, $C_2$-$C_6$ alkenyl or $C_2$-$C_6$ alkynyl, wherein the alkyl, alkenyl or alkynyl is substituted with a radioactive halo. As an example of this embodiment, $R^1$ is —OH or $C_1$-$C_6$ alkoxy; $R^2$ is hydrogen; $R^3$ is hydrogen or $C_1$-$C_6$ alkyl; and $R^4$ is $C_1$-$C_6$ alkyl substituted with $^{18}F$. As another example, $R^1$ is —OH; $R^3$ is hydrogen; and $R^4$ is —$CH_2CH_2CH_2^{18}F$.

In yet another embodiment, the inventive compound bind selectively to amyloid, particularly synthetic Aβ in vitro or Aβ deposited in neuritic plaques; cross a non-compromised blood-brain barrier in vivo; are bioavailable; and/or are non-toxic.

Methods of Use

The inventive compound may be used to determine the presence, location and/or amount of one or more amyloid deposit(s) in an organ or body area, including the brain, of an animal. Amyloid deposit(s) include, without limitation, deposit(s) of Aβ. In allowing the temporal sequence of amyloid deposition to be followed, the inventive compound may further be used to correlate amyloid deposition with the onset of clinical symptoms associated with a disease, disorder or condition. The inventive compound may ultimately be used to assess the efficacy of a treatment for amyloid deposition, and to diagnose a disease, disorder or condition characterized by amyloid deposition, such as AD, familial AD, Down's syndrome, amyloidosis, Type II diabetes mellitus, Mild Cognitive Impairment (MCI) and homozygotes for the apolipoprotein E4 allele.

Method for Detecting Amyloid Deposit(s) In Vivo

This invention further provides a method for detecting amyloid deposit(s) in vivo, comprising:

(i) administering to an animal an effective amount of an inventive compound, wherein the compound would bind to any amyloid deposit(s) in the animal; and (ii) detecting binding of the compound to amyloid deposit(s) in the animal.

After a sufficient time has elapsed for the compound to bind with the amyloid deposit(s), for example 30 minutes to 48 hours following administration, the binding may be detected by any means known in the art. Examples of detection means include, without limitation, assays (such as immunometric, calorimetric, densitometric, spectrographic and chromatographic assays), non-invasive neuroimaging techniques (such as magnetic resonance spectroscopy (MRS), magnetic resonance imaging (MRI), and gamma imaging techniques such as single-photon emission computed tomography (SPECT) and positron emission tomography (PET). For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of labeled compound along with a large excess of unlabeled, but otherwise chemically identical compound.

The type of detection instrument available may be a factor in selecting the radioactive halo or carbon isotope. For instance, the selected radioisotope should have a type of decay that is detectable by a given instrument. Another consideration relates to the half-life of the radioisotope. The half-life should be long enough such that the radioisotope is still detectable at the time of maximum uptake by the target, but short enough such that the host does not sustain deleterious radiation. For SPECT detection, the selected radioisotope may lack a particulate emission, but may produce a large number of photons in the 140-200 keV range. For PET detection, the selected radioisotope may be a positron-emitting radioisotope, which annihilates to form two 511 keV gamma rays detectable by a PET camera.

Useful radioisotopes include, without limitation: $^{125}I$, $^{14}C$, and $^3H$ for in vitro quantification of amyloid in homogenates of biopsy or post-mortem tissue; $^{11}C$ and $^{18}F$ for PET in vivo imaging; $^{123}I$ for SPECT imaging; $^{18}F$ for MRS/MRI; $^3H$ or $^{14}C$ for in vitro studies; and $^{18}F$ and $^{13}C$ for magnetic resonance spectroscopy. In one embodiment, the detecting is effected by gamma imaging, magnetic resonance imaging or magnetic resonance spectroscopy. In another embodiment, the gamma imaging is PET or SPECT.

The inventive compound may be administered by any means known to one of ordinary skill in the art. For example, administration to the animal may be local or systemic and accomplished orally, parenterally, by inhalation spray, topically, rectally, nasally, buccally, vaginally, or via an implanted reservoir. The term "parenteral" as used herein includes subcutaneous, intravenous, intraarterial, intramuscular, intraperitoneal, intrathecal, intraventricular, intrasternal, intracranial, and intraosseous injection and infusion techniques. The exact administration protocol will vary depending upon various factors including the age, body weight, general health, sex and diet of the patient; the determination of specific administration procedures would be routine to an one of ordinary skill in the art.

Dose levels on the order of about 0.001 μg/kg/day to about 10,000 mg/kg/day of an inventive compound are useful for the inventive methods. In one embodiment, the dose level is about 0.001 μg/kg/day to about 10 μg/kg/day. In another embodiment, the dose level is about 0.01 μg/kg/day to about 1.0 μg/kg/day. In yet another embodiment, the dose level is about 0.1 mg/kg/day to about 100 mg/kg/day.

The specific dose level for any particular patient will vary depending upon various factors, including the activity and the possible toxicity of the specific compound employed; the age, body weight, general health, sex and diet of the patient; the time of administration; the rate of excretion; the drug combination; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods. The regimen may include pretreatment and/or co-administration with additional therapeutic agent(s).

In one embodiment, the inventive compound is administered to an animal that is suspected of having or that is at risk of developing a disease, disorder or condition characterized by amyloid deposition. For example, the animal may be an elderly human.

In another embodiment, the inventive compound binds to Aβ with a dissociation constant ($K_D$) of about 0.0001 μM to about 10.0 μM when measured by binding to synthetic Aβ peptide or AD brain tissue.

Method for Detecting Amyloid Deposit(s) In Vitro

This invention further provides a method for detecting amyloid deposit(s) in vitro comprising:

(i) contacting a bodily tissue with an effective amount of an inventive compound, wherein the compound would bind any amyloid deposit(s) in the tissue; and (ii) detecting binding of the compound to amyloid deposit(s) in the tissue.

The binding may be detected by any means known in the art. Examples of detection means include, without limitation, microscopic techniques, such as bright-field, fluorescence, laser-confocal and cross-polarization microscopy.

In one embodiment, the tissue is biopsy or post-mortem tissue that is formalin-fixed or fresh-frozen. In another embodiment, the tissue is homogenized. In yet another embodiment, the inventive compound is in a solution that further comprises 25-99% ethanol, with the remainder of the solution being water. In yet another embodiment, the solution comprises 0-50% ethanol and 0.0001 to 100 µM of the compound. In yet another embodiment, the method further comprises (iii) separating from the tissue the amyloid deposit(s) bound to the compound; and (iv) quantifying the amyloid deposit(s) bound to the inventive compound. The bound amyloid deposit(s) may be separated from the tissue by any means known in the art, such as filtering. The amount of bound amyloid deposit(s) may be converted to units of µg of amyloid deposit(s) per 100 mg of tissue by comparison to a standard curve generated by incubating known amounts of amyloid with the inventive compound or pharmaceutically acceptable salt, hydrate, solvate or prodrug.

Method for Distinguishing Alzheimer's Diseased Brain from Normal Brain

This invention further provides a method for distinguishing an Alzheimer's diseased brain from a normal brain comprising:

(i) obtaining tissues from (i) the cerebellum and (ii) another area of the same brain, of a normal animal and of an animal suspected of having Alzheimer's disease;

(ii) contacting the tissues with an inventive compound;

(iii) quantifying the amyloid bound to the compound;

(iv) calculating the ratio of the amount of amyloid in the area of the brain other than the cerebellum to the amount of amyloid in the cerebellum;

(v) comparing the ratio for a normal animal with the ratio for an animal suspected of having Alzheimer's disease.

A diagnosis of Alzheimer's disease may be made if the ratio for an animal suspected of having Alzheimer's disease is, for example, above 90% of the ratio for a normal animal. For this method, a "normal" animal is one that is not suffering from Alzheimer's disease.

Pharmaceutical Compositions

This invention further provides a pharmaceutical composition comprising:

(i) an effective amount of an inventive compound; and (ii) a pharmaceutically acceptable carrier.

The composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and therapeutic agent(s).

The composition may be formulated into solid, liquid, gel or suspension form for: (1) oral administration as, for example, a drench (aqueous or non-aqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by subcutaneous, intramuscular, intravenous or epidural injection as, for example, a sterile solution, suspension or sustained-release formulation; (3) topical application as, for example, a cream, ointment, controlled-release patch or spray applied to the skin; (4) intravaginal or intrarectal administration as, for example, a pessary, cream or foam; (5) sublingual administration; (6) ocular administration; (7) transdermal administration; or (8) nasal administration.

In one embodiment, the composition is formulated for intravenous administration and the carrier includes a fluid and/or a nutrient replenisher. In another embodiment, the composition is capable of binding specifically to amyloid in vivo, is capable of crossing the blood-brain barrier, is non-toxic at appropriate dose levels and/or has a satisfactory duration of effect. In yet another embodiment, the composition comprises about 10 mg of human serum albumin and from about 0.5 to 500 mg of the inventive compound per milliliter of phosphate buffer containing NaCl.

EXAMPLES

Example 1

Compounds of Formula I can be Synthesized According to the Following General Method 6-substituted 2-aminobenzothiazole of the form

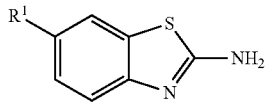

wherein $R^1$ is hydrogen, —OH, —NO$_2$, —CN, —COOR, —OCH$_2$OR, $C_1$-$C_6$ alkyl, $C_2$-$C_6$ alkenyl, $C_2$-$C_6$ alkynyl, $C_1$-$C_6$ alkoxy or halo is hydrolysed by one of the following two procedures:

General Procedure of 2-Aminothiophenol Via Hydrolysis:

The 6-substituted 2-aminobenzothiazole (172 mmol) is suspended in 50% KOH (180 g KOH dissolved in 180 mL water) and ethylene glycol (40 mL). The suspension is heated to reflux for 48 hours. Upon cooling to room temperature, toluene (300 mL) is added and the reaction mixture is neutralized with acetic acid (180 mL). The organic layer is separated and the aqueous layer is extracted with another 200 mL of toluene. The toluene layers are combined and washed with water and dried over MgSO$_4$. Evaporation of the solvent gives the desired product.

General Procedure of 2-Aminothiophenol Via Hydrazinolysis:

The 6-substituted-benzothiazole (6.7 mmol) is suspended in ethanol (11 mL, anhydrous) and hydrazine (2.4 mL) is added under a nitrogen atmosphere at room temperature. The reaction mixture is heated to reflux for 1 hour. The solvent is evaporated and the residue is dissolved into water (10 mL) and adjusted to a pH of 5 with acetic acid. The precipitate is collected with filtration and washed with water to give the desired product.

The resulting 5-substituted-2-amino-1-thiophenol of the form

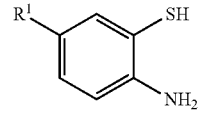

is coupled to a benzoic acid of the form:

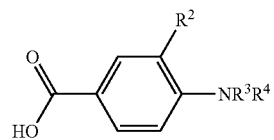

wherein $R^2$ is hydrogen, and $R^3$ and $R^4$ are independently hydrogen, $C_1$-$C_6$ alkyl, $C_2$-$C_6$ alkenyl or $C_2$-$C_6$ alkynyl
by the following reaction:

A mixture of the 5-substituted 2-aminothiophenol (4.0 mmol), the benzoic acid (4.0 mmol), and polyphosphoric acid (PPA) (10 g) is heated to 220° C. for 4 hours. The reaction mixture is cooled to room temperature and poured into 10% potassium carbonate solution (~400 mL). The precipitate is collected by filtration under reduced pressure to give the desired product, which can be purified by flash chromatography or recrystallization.

The $R^2$ hydrogen can be substituted with either a non-radioactive halo or a radioactive halo by the following reaction:

To a solution of 6-substituted 2-(4'-aminophenyl)-benzothiazole (1 mg) in 250 μL acetic acid in a sealed vial is added 40 μL of chloramine-T solution (28 mg dissolved in 500 μL acetic acid) followed by 27 μL (ca. 5 mCi) of sodium [$^{125}$I]iodide (specific activity 2,175 Ci/mmol). The reaction mixture is stirred at room temperature for 2.5 hours and quenched with saturated sodium hydrogensulfite solution. After dilution with 20 ml of water, the reaction mixture is loaded onto C8 Plus SepPak and eluted with 2 ml methanol. Depending on the nature of the substituent on the 6-position, protecting groups may need to be employed. For example, the 6-hydroxy group is protected as the methanesulfonyl (mesyloxy) derivative. For deprotection of the methanesulfonyl group, 0.5 ml of 1 M NaOH is added to the eluted solution of radioiodinated intermediate. The mixture is heated at 50° C. for 2 hours. After being quenched by 500 μL of 1 M acetic acid, the reaction mixture is diluted with 40 mL of water and loaded onto a C8 Plus SepPak. The radioiodinated product, having a radioactivity of ca. 3 mCi, is eluted off the SepPak with 2 mL of methanol. The solution is condensed by a nitrogen stream to 300 μL and the crude product is purified by HPLC on a Phenomenex ODS column (MeCN/TEA buffer, 35:65, pH 7.5, flow rate 0.5 mL/minute up to 4 minutes, 1.0 mL/minute at 4-6 minutes, and 2.0 mL/minute after 6 minutes, retention time 23.6). The collected fractions are loaded onto a C8 Plus SepPak. Elution with 1 mL of ethanol gave ca. 1 mCi of the final radioiodinated product.

When either or both $R^3$ and $R^4$ are hydrogen, then $R^3$ and $R^4$ can be converted to $C_1$-$C_6$ alkyl, $C_2$-$C_6$ alkenyl or $C_2$-$C_6$ alkynyl by reaction with an alkyl, alkenyl or alkynyl halide under the following conditions:

For dialkylation: To a solution of 6-substituted 2-(4'-aminophenyl)-benzothiazole (0.59 mmol) in DMSO (anhydrous, 2 ml) are added alkyl, alkenyl, or alkynyl halide (2.09 mmol), and $K_2CO_3$ (500 mg, 3.75 mmol). The reaction mixture is heated at 140° C. for 16 hours. Upon cooling to room temperature, the reaction mixture is poured into water and extracted with ethyl acetate (3×10 mL). The organic layers are combined and the solvent is evaporated. The residue is purified by flash column to give the desired 6-substituted dimethylaminophenyl)-benzothiazole.

For monoalkylation: To a solution of 6-substituted 2-(4'-aminophenyl)-benzothiazole (0.013 mmol) in DMSO (anhydrous, 0.5 ml) is added alkyl, alkenyl, or alkynyl halide (0.027 mmol) and anhydrous $K_2CO_3$ (100 mg, 0.75 mmol). The reaction mixture is heated at 100° C. for 16 hours. Upon cooling to room temperature, the reaction mixture is directly purified by normal phase preparative TLC to give the desired 6-substituted-2-(4'-methylaminophenyl)-benzothiazole derivatives.

When $R^2$ is hydrogen or a non-radioactive halo, $R^4$ is $C_1$-$C_6$ alkyl, $C_2$-$C_6$ alkenyl or $C_2$-$C_6$ alkynyl, wherein the alkyl, alkenyl or alkynyl comprises a radioactive carbon or is substituted with a radioactive halo, the compound can be synthesized by one of the following sequences:

For radioactive carbon incorporation:

Approximately 1 Ci of [$^{11}$C]carbon dioxide is produced using a CTI/Siemens RDS 112 negative ion cyclotron by irradiation of a nitrogen gas ($^{14}N_2$) target containing 1% oxygen gas with a 40 μA beam current of 11 MeV protons for 60 minutes. [$^{11}$C]Carbon dioxide is converted to [$^{11}$C]methyl iodide by first reacting it with a saturated solution of lithium aluminum hydride in THF followed by the addition of hydriodic acid at reflux temperature to generate [$^{11}$C]methyl iodide. The [$^{11}$C]methyl iodide is carried in a stream of nitrogen gas to a reaction vial containing the precursor for radiolabeling. The precursor, 6-substituted 2-(4'-aminophenyl)-benzothiazole (~3.7 μmoles), is dissolved in 400 μL of DMSO. Dry KOH (10 mg) is added, and the 3 mL V-vial is vortexed for 5 minutes. No-carrier-added [$^{11}$C]methyl iodide is bubbled through the solution at 30 mL/minute at room temperature. The reaction is heated for 5 minutes at 95° C. using an oil bath. The reaction product is purified by semi-preparative HPLC using a Prodigy ODS-Prep column eluted with 60% acetonitrile/40% triethylammonium phosphate buffer pH 7.2 (flow at 5 mL/minute for 0-7 minutes then increased to 15 mL/minute for 7-30 minutes). The fraction containing [N-methyl-$^{11}$C] 6-substituted 2-(4'-methylaminophenyl)-benzothiazole (at about 15 min) is collected and diluted with 50 mL of water and eluted through a Waters C18 SepPak Plus cartridge. The C18 SepPak is washed with 10 mL of water, and the product is eluted with 1 mL of ethanol (absolute) into a sterile vial followed by 14 mL of saline. Radiochemical and chemical purities are >95% as determined by analytical HPLC (k'=4.4 using the Prodigy ODS(3) analytical column eluted with 65/35 acetonitrile/triethylammonium phosphate buffer pH 7.2). The radiochemical yield averages 17% at EOS based on [$^{11}$C]methyl iodide, and the specific activity averages about 160 GBq/μmol (4.3 Ci/μmol) at end of synthesis.

For radioactive halogen incorporation:

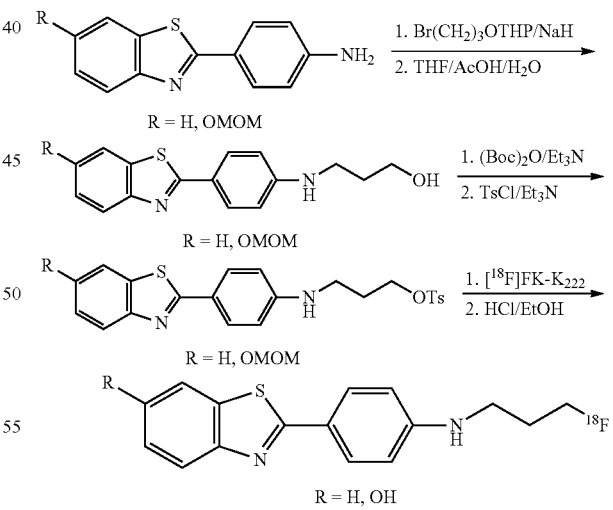

A mixture of 6-substituted 2-(4'-aminophenyl)-benzathiazole (protecting groups may be necessary depending on the nature of the 6-substituent as noted above) (0.22 mmol), NaH (4.2 mmol) and 2-(-3-bromopropoxy)tetrahydro-2-H-pyran (0.22 mmol) in THF (8 mL) is heated to reflux for 23 hours. The solvent is removed by distillation and the residue is dissolved in to ethyl acetate and water, the organic layer is separated and the aqueous layer is extracted with ethyl acetate (10 mL×6). The organic layer is combined and dried over MgSO₄ and evaporated to dryness. The residue is added AcOH/THF/H₂O solution (5 mL, 4/2/1) and heated to 100° C. for 4 hours. The solvent is removed by evaporation and the residue is dissolved in ethyl acetate (~10 mL) washed by NaHCO₃ solution, dried over MgSO₄ and evaporated to dryness to give a residue which is purified with preparative TLC(hexane:ethyl acetate=60:40) to give the desired 6-substituted 2-(4'-(3"-hydroxypropylamino)-phenyl)-benzothiazole (45%).

To a solution of 6-substituted 2-(4'-(3"-hydroxypropylamino)-phenyl)-benzathiazole (0.052 mmol) and Et₃N(0.5 ml) dissolved in acetone (5 mL) is added (Boc)₂O (50 mg, 0.22 mmol). The reaction mixture is stirred at room temperature for 6 hours followed by addition of tosyl chloride (20 mg, 0.11 mmol). The reaction mixture is stirred at room temperature for another 24 hours. The solvent is removed and the residue is dissolved into ethyl acetate (10 mL), washed with NaCO₃ solution, dried over MgSO₄, evaporated, and purified with flash column (Hexane/ethyl acetate=4/1) to give the desired 6-substituted 2-(4'-(3"-toluenesulfonoxypropylamino)-phenyl)-benzothiazole (13%). This 6-substituted 2-(4'-(3"-toluenesulfonoxypropylamino)-phenyl)-benzothiazole is then radiofluorinated by standard methods as follows:

A cyclotron target containing 0.35 mL of 95% [0-18]-enriched water is irradiated with 11 MeV protons at 20 μA of beam current for 60 minutes, and the contents are transferred to a 5 mL reaction vial containing Kryptofix 222 (22.3 mg) and K₂CO₃ (7.9 mg) in acetonitrile (57 μL). The solution is evaporated to dryness three times at 110° C. under a stream of argon following the addition of 1 mL aliquots of acetonitrile. To the dried [F-18]fluoride is added 3 mg of 6-substituted 2-(4'-(3"-toluenesulfonoxypropylamino)-phenyl)-benzothiazole in 1 mL DMSO, and the reaction vial is sealed and heated to 85° C. for 30 minutes. To the reaction vial, 0.5 mL of MeOH/HCl (concentrated) (2/1 v/v) is added, and the vial is heated at 120° C. for 10 minutes. After heating, 0.3 mL of 2 M sodium acetate buffer is added to the reaction solution followed by purification by semi-prep HPLC using a Phenomenex Prodigy ODS-prep C18 column (10 μm 250×10 mm) eluted with 40% acetonitrile/60% 60 mM triethylaminephosphate buffer (v/v) pH 7.2 at a flow rate of 5 mL/minute for 15 minutes, then the flow is increased to 8 mL/minute for the remainder of the separation. The product, [F-18] 6-substituted 2-(4'-(3"-fluoropropylamino)-phenyl)-benzothiazole, is eluted at ~20 minutes in a volume of about 16 mL. The fraction containing [F-18] 6-substituted 2-(4'-(3"-fluoropropylamino)-phenyl)-benzothiazole is diluted with 50 mL of water and eluted through a Waters C18 SepPak Plus cartridge. The SepPak cartridge is then washed with 10 mL of water, and the product is eluted using 1 mL of ethanol (absol.) into a sterile vial. The solution is diluted with 10 mL of sterile normal saline for intravenous injection into animals. The [F-18]6-substituted 2-(4'-(3"-fluoropropylamino)-phenyl)-benzothiazole product is obtained in 2-12% radiochemical yield at the end of the 120 minute radiosynthesis (not decay corrected) with an average specific activity of 1500 Ci/mmol.

Example 2

[N-Methyl-¹¹C]2-(4'-Dimethylaminophenyl)-6-Methoxy-Benzothiazole was Synthesized According to Scheme I

SCHEME I

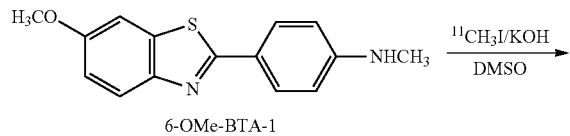

6-OMe-BTA-1

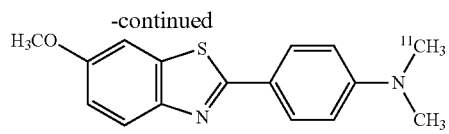

[N-methyl-¹¹C]2-(4'-Dimethylaminophenyl)-6-methoxy-benzothiazole

Approximately 1 Ci of [¹¹C]carbon dioxide was produced using a CTI/Siemens RDS 112 negative ion cyclotron by irradiation of a nitrogen gas (¹⁴N₂) target containing 1% oxygen gas with a 40 μA beam current of 11 MeV protons for 60 minutes. [¹¹C]Carbon dioxide is converted to [¹¹C]methyl iodide by first reacting it with a saturated solution of lithium aluminum hydride in THF followed by the addition of hydriodic acid at reflux temperature to generate [¹¹C]methyl iodide. The [¹¹C]methyl iodide is carried in stream of nitrogen gas to a reaction vial containing the precursor for radiolabeling. The precursor, 6-CH₃O-BTA-1 (1.0 mg, 3.7 μmoles), was dissolved in 400 μL of DMSO. Dry KOH (10 mg) was added, and the 3 mL V-vial was vortexed for 5 minutes. No-carrier-added [¹¹C]methyl iodide was bubbled through the solution at 30 mL/minute at room temperature. The reaction was heated for 5 minutes at 95° C. using an oil bath. The reaction product was purified by semi-preparative HPLC using a Prodigy ODS-Prep column eluted with 60% acetonitrile/40% triethylammonium phosphate buffer pH 7.2 (flow at 5 mL/minute for 0-7 minutes then increased to 15 mL/minute for 7-30 minutes). The fraction containing [N-Methyl-¹¹C]2-(4'-Dimethylaminophenyl)-6-methoxy-benzothiazole (at about 15 minutes) was collected and diluted with 50 mL of water and eluted through a Waters C18 SepPak Plus cartridge. The C18 SepPak was washed with 10 mL of water, and the product was eluted with 1 mL of ethanol (absolute) into a sterile vial followed by 14 mL of saline. Radiochemical and chemical purities were >95% as determined by analytical HPLC (k'=4.4 using the Prodigy ODS(3) analytical column eluted with 65/35 acetonitrile/triethylammonium phosphate buffer pH 7.2). The radiochemical yield averaged 17% at EOS based on [¹¹C]methyl iodide, and the specific activity averaged about 160 GBq/μmol (4.3 Ci/μmol) at end of synthesis.

Example 3

2-(3'-¹²⁵I-Iodo-4'-Amino-Phenyl)-Benzothiazol-6-Ol was Synthesized According to Scheme II

SCHEME II

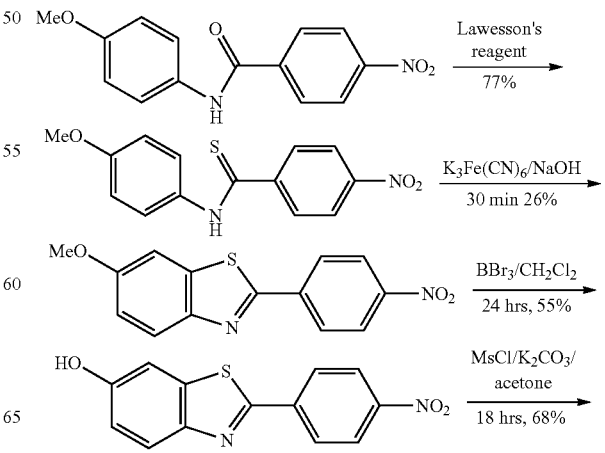

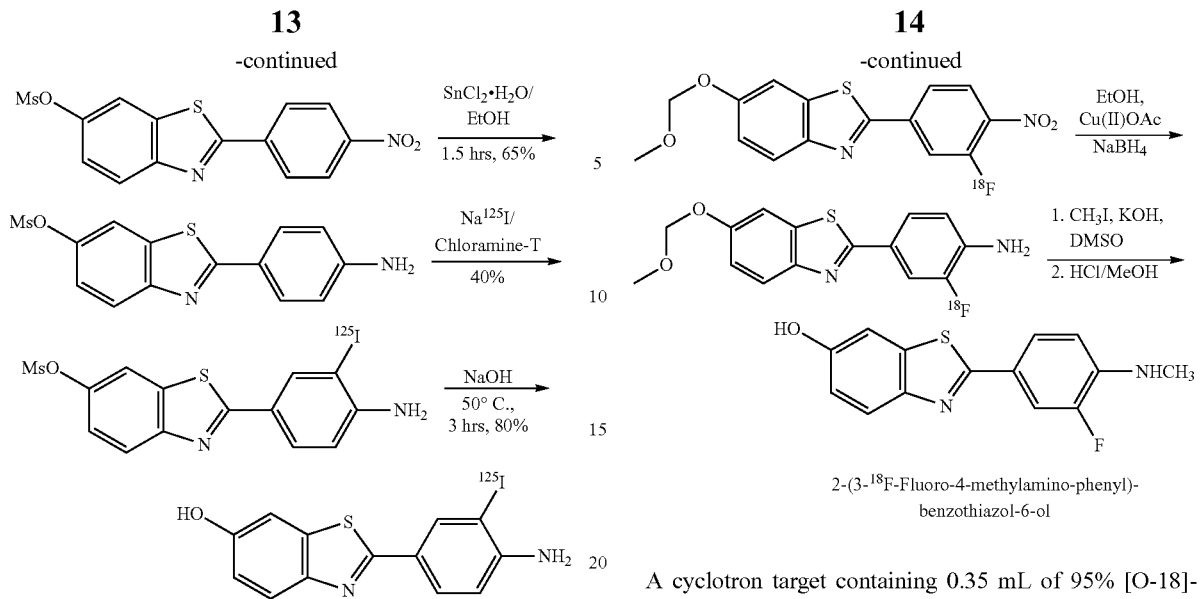

To a solution of 2-(4'-aminophenyl)-6-methanesulfonoxy-benzothiazole (1 mg) in 250 μL acetic acid in a sealed vial was added 40 μL of chloramine-T solution (28 mg dissolved in 500 μL acetic acid) followed by 27 μL (ca. 5 mCi) of sodium [$^{125}$I]iodide (specific activity 2,175 Ci/mmol). The reaction mixture was stirred at room temperature for 2.5 hours and quenched with saturated sodium hydrogensulfite solution. After dilution with 20 ml of water, the reaction mixture was loaded onto C8 Plus SepPak and eluted with 2 ml methanol. For deprotection of the methanesulfonyl group, 0.5 ml of 1 M NaOH was added to the eluted solution of radioiodinated intermediate. The mixture was heated at 50° C. for 2 hours. After being quenched by 500 μL of 1 M acetic acid, the reaction mixture was diluted with 40 mL of water and loaded onto a C8 Plus SepPak. The radioiodinated product, having a radioactivity of ca. 3 mCi, was eluted off the SepPak with 2 mL of methanol. The solution was condensed by a nitrogen stream to 300 μL and the crude product was purified by HPLC on a Phenomenex ODS column (MeCN/TEA buffer, 35:65, pH 7.5, flow rate 0.5 mL/minute up to 4 minutes, 1.0 mL/minute at 4-6 minutes, and 2.0 mL/minute after 6 minutes, retention time 23.6). The collected fractions were loaded onto a C8 Plus SepPak. Elution with 1 mL of ethanol gave ca. 1 mCi of the final radioiodinated product.

Example 4

2-(3-$^{18}$F-Fluoro-4-Methylamino-Phenyl)-Benzothiazol-6-Ol was Synthesized According to Scheme III

SCHEME III

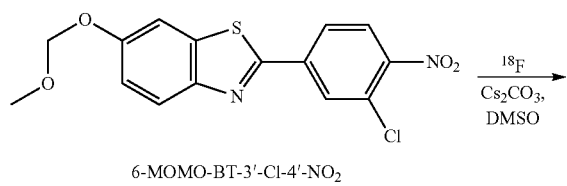

6-MOMO-BT-3'-Cl-4'-NO$_2$

A cyclotron target containing 0.35 mL of 95% [O-18]-enriched water was irradiated with II MeV protons at 20 μA of beam current for 60 minutes, and the contents were transferred to a 5 mL reaction vial containing 2 mg Cs$_2$CO$_3$ in acetonitrile (57 μL). The solution was evaporated to dryness at 110° C. under a stream of argon three times using 1 mL aliquots of acetonitrile. To the dried [F-18]fluoride was added 6 mg of 6-MOMO-BT-3'-Cl-4'-NO$_2$ in 1 mL DMSO, and the reaction vial was sealed and heated to 120° C. for 20 minutes (radiochemical incorporation for this first radiosynthesis step was about 20% of solubilized [F-18]fluoride). To the crude reaction mixture was added 8 mL of water and 6 mL of diethyl ether, the mixture was shaken and allowed to separate. The ether phase was removed and evaporated to dryness under a stream of argon at 120° C. To the dried sample, 0.5 mL of absolute EtOH was added along with 3 mg copper (II) acetate and 8 mg of NaBH$_4$. The reduction reaction was allowed to proceed for 10 minutes at room temperature (the crude yield for the reduction step was about 40%). To the reaction mixture was added 8 mL of water and 6 mL of diethyl ether, the mixture was shaken and the ether phase separated. The diethyl ether phase was dried under a stream of argon at 120° C. To the reaction vial, 700 uL of DMSO was added containing 30 micromoles of CH$_3$I and 20 mg of dry KOH. The reaction vial was heated at 120° C. for 10 minutes. A solution of 700 uL of 2:1 MeOH/HCl (concentrated) was added and heated for 15 minutes at 120° C. After heating, 1 mL of 2 M sodium acetate buffer was added to the reaction solution followed by purification by semi-prep HPLC using a Phenomenex Prodigy ODS-prep C18 column (10 μm 250×10 mm) eluted with 35% acetonitrile/65% 60 mM triethylamine-phosphate buffer (v/v) pH 7.2 at a flow rate of 5 mL/minute for 2 minutes, then the flow was increased to 15 mL/minute for the remainder of the separation. The product, 2-(3-$^{18}$F-fluoro-4-methylamino-phenyl)-benzothiazol-6-ol, eluted at 15 minutes in a volume of about 16 mL. The fraction containing 2-(3-$^{18}$F-fluoro-4-methylamino-phenyl)-benzothiazol-6-ol was diluted with 50 mL of water and eluted through a Waters C18 SepPak Plus cartridge. The SepPak cartridge was then washed with 10 mL of water, and the product was eluted using 1 mL of ethanol (absol.) into a sterile vial. The solution was diluted with 10 mL of sterile normal saline for intravenous injection into animals. The 2-(3-$^{18}$F-fluoro-4-methylamino-phenyl)-benzothiazol-6-ol product was obtained in 0.5% (n=4) radiochemical yield at the end of the 120 minute radiosynthesis (not decay corrected) with an average specific activity of 1000 Ci/mmol. The radiochemical and chemical purities of 2-(3-$^{18}$F-fluoro-4-methylamino-phenyl)-benzothiazol-6-ol were assessed by radio-HPLC with UV detection at 350 nm using a Phenomenex Prodigy ODS(3) C18 column (5 μm, 250×4.6 mm) eluted with 40% acetonitrile/60% 60 mM triethylamine-phosphate buffer (v/v) pH 7.2. 2-(3-$^{18}$F-Fluoro-4-methylamino-phenyl)-benzothiazol-6-ol had a retention time of ~11 minutes at a flow rate of 2 mL/min (k'=5.5). The radiochemical purity was >99%, and the chemical purity was >90%. The radiochemical identity of 2-(3-$^{18}$F-Fluoro-4-methylamino-phenyl)-benzothiazol-6-ol was confirmed by reverse phase radio-HPLC utilizing a quality control sample of the final radiochemical product co-injected with a authentic (cold) standard.

Example 5

2-[4-(3-$^{18}$F-Fluoro-Propylamino)-Phenyl]-Benzothiazol-6-Ol was Synthesized According to Scheme IV

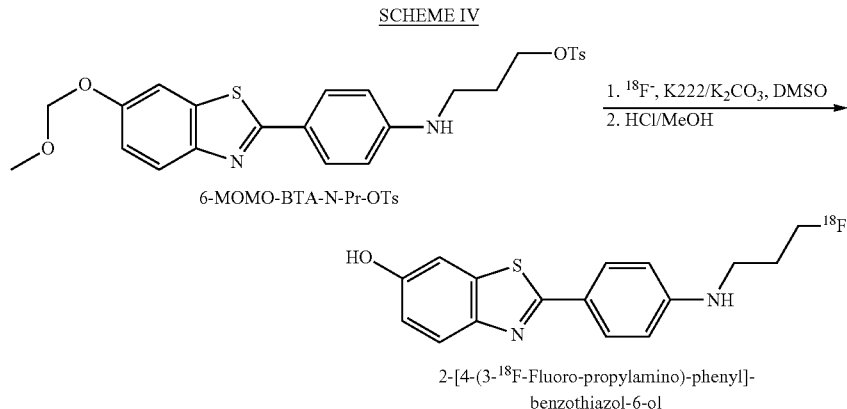

A cyclotron target containing 0.35 mL of 95% [O-18]-enriched water was irradiated with 11 MeV protons at 20 μA of beam current for 60 minutes, and the contents were transferred to a 5 mL reaction vial containing Kryptofix 222 (22.3 mg) and K$_2$CO$_3$ (7.9 mg) in acetonitrile (57 μL). The solution was evaporated to dryness three times at 110° C. under a stream of argon following the addition of 1 mL aliquots of acetonitrile. To the dried [F-18]fluoride was added 3 mg of 6-MOMO-BTA-N-Pr-OTs in 1 mL DMSO, and the reaction vial was sealed and heated to 85° C. for 30 minutes. To the reaction vial, 0.5 mL of MeOH/HCl (concentrated) (2/1 v/v) was added, and the vial was heated at 120° C. for 10 minutes. After heating, 0.3 mL of 2 M sodium acetate buffer was added to the reaction solution followed by purification by semi-prep HPLC using a Phenomenex Prodigy ODS-prep C18 column (10 μm 250×10 mm) eluted with 40% acetonitrile/60% 60 mM triethylamine-phosphate buffer (v/v) pH 7.2 at a flow rate of 5 mL/minute for 15 minutes, then the flow was increased to 8 mL/minute for the remainder of the separation. The product, [F-18]6-HO-BTA-N-PrF, eluted at ~20 minutes in a volume of about 16 mL. The fraction containing [F-18]6-HO-BTA-N-PrF was diluted with 50 mL of water and eluted through a Waters C18 SepPak Plus cartridge. The SepPak cartridge was then washed with 10 mL of water, and the product was eluted using 1 mL of ethanol (absol.) into a sterile vial. The solution was diluted with 10 mL of sterile normal saline for intravenous injection into animals. The [F-18]6-HO-BTA-N-PrF product was obtained in 8±4% (n=8) radiochemical yield at the end of the 120 minute radiosynthesis (not decay corrected) with an average specific activity of 1500 Ci/mmol. The radiochemical and chemical purities of [F-18]6-HO-BTA-N-PrF were assessed by radio-HPLC with UV detection at 350 nm using a Phenomenex Prodigy ODS(3) C18 column (5 μm, 250×4.6 mm) eluted with 40% acetonitrile/60% 60 mM triethylamine-phosphate buffer (v/v) pH 7.2. [F-18]6-HO-BTA-N-PrF had a retention time of ~12 minutes at a flow rate of 2 mL/minute (k'=6.1). The radiochemical purity was >99%, and the chemical purity was >90%. The radiochemical identity of [F-18]6-HO-BTA-N-PrF was confirmed by reverse phase radio-HPLC utilizing a quality control sample of the final radiochemical product co-injected with a authentic (cold) standard.

Example 6

In Vivo Mouse Brain Entry Studies

Experiments to assess brain penetration of 2-(3'-$^{125}$I-iodo-4'-amino-phenyl)-benzothiazol-6-ol (Compound A), 2-(3-[$^{18}$F]-fluoro-4-methylamino-phenyl)-benzothiazol-6-ol (Compound B), and 2-[4-(3-$^{18}$F-fluoro-propylamino)-phenyl]benzothiazol-6-ol (Compound C) were performed in young, wild type mice that had no amyloid deposits in their brain. This study reflects brain entry and clearance from normal brain tissue. A necessary criterion for a good PET imaging agent is rapid clearance from brain areas that do not contain the targeted binding site. A measure of non-specific binding clearance rate is provided by the ratio of the 2 minutes-to-30 minutes (% ID-kg)/g values.

Studies were performed in female Swiss-Webster mice (23-35 g) in accordance with the Guide for the Care and Use of Laboratory Animals adopted by NIH and with the approval of the local Institutional Animal Care and Use Committee. The mice were injected in a lateral tail vein with 0.37-3.7 MBq (10-100 μCi) of a high specific activity (~2.0/μmol) Compound A, Compound B or Compound C contained in <0.10 mL of a solution of 95% isotonic saline and 5% ethanol. The mice were anesthetized and killed by cardiac excision following cardiac puncture to obtain arterial blood samples at 2 minutes or 30 minutes post-injection. The mouse brains were rapidly excised and divided into the cerebellum and the remaining whole brain (including brain stem) fractions. The brain samples were counted in a gamma well-counter, and the counts were decay-corrected to the time of injection relative to $^{125}$I or $^{18}$F standards prepared from the injection solution to determine the percent injected dose (% ID) in the samples. The brain samples were weighed to determine the percent injected dose per gram tissue (% ID/g), and this quantity was multiplied by the whole body weight (in kg) to determine the body-weight normalized radioactivity concentration [(% ID-kg)/g] of each tissue sample. Compound A, Compound B and Compound C displayed relatively high brain entry at early time points and fast clearance at later time points. The radioactivity concentrations (% ID-kg/g) at 2 minutes and 30 minutes and the 2 minutes-to-30 minutes ratios are presented in Table I below.

TABLE I

|  | Radioactivity Conc. at 2 min. (% ID-kg/g) | Radioactivity Conc. at 30 min. (% ID-kg/g) | 2 min./30 min. Ratio |
| --- | --- | --- | --- |
| Compound A | 0.141 | 0.009 | 16 |
| Compound B | 0.29 | 0.030 | 10 |
| Compound C | 0.17 | 0.011 | 16 |

Example 7

In Vivo Baboon Imaging Studies

PET imaging studies in adult baboons (*Papio anubis*) (weight 15-35 kg, ages 6-12 years) were performed with Compound B and Compound C in accordance with the Guide for the Care and Use of Laboratory Animals adopted by NIH and with the approval of the local Institutional Animal Care and Use Committee. Prior to PET imaging, the animals were initially sedated with ketamine (10-15 mg/kg, i.m.), given atropine (0.5 mg, i.m.) to control salivation and heart rate, and intubated. The baboons were subsequently maintained on a ventilator with isofluorane (0.5-1.25%) anesthesia and medical air. Pancuronium bromide was administered as necessary (intravenously, up to 0.06 mg/kg/hour, titrated to effect) to keep the animals immobilized during the study. A femoral artery catheter was inserted to monitor blood pressure and sample arterial blood, and an intravenous catheter was placed in an antecubital vein for radiotracer injection and to administer fluids as necessary throughout the course of the imaging study. Blood pressure, heart and respiratory rates, and expired $CO_2$ and oxygen saturation levels were monitored continuously during the PET studies. The baseline rectal body temperature (~37° C.) was maintained using a heating blanket (Gaymar, Orchard Park, N.Y.) and temperature regulator (Yellow Springs Instruments, Yellow Springs, Ohio). Prior to scanning, the baboon's head was fixed so that the image planes were acquired approximately parallel to the orbital-meatal line.

PET data were acquired using an ECAT HR+PET scanner (CTI PET Systems, Knoxville, Tenn.) in 3D imaging mode (63 parallel slices; 15.2 cm axial field-of-view; 4.1 mm full-width half-maximum in-plane resolution). A Neuro-Insert (CTI PET Systems) was used to reduce the contribution of scattered photon events. After the baboons were positioned in the PET scanner, a windowed transmission scan (10-15 minutes) was obtained for attenuation correction of the PET emission data using rotating $^{68}$Ge/$^{68}$Ga rods. Compound B and Compound C were administered intravenously over 20 seconds, and a dynamic series of PET scans were acquired over 90 minutes using 26 frames of increasing length (6×20 seconds; 4×30 seconds; 6×60 seconds; 4×5 minutes; 6×10 minutes). Approximately 185 MBq (~5 mCi) of a high specific activity (>14.8 GBq/μmol) Compound B or Compound C was injected in a baboon. In other studies, 148-296 MBq (4-8 mCi) of a high specific activity (>18.5 GBq/μmol) reference PET radiotracer was injected, including either [$^{11}$C] (+)-McN5652, [carbonyl-$^{11}$C]WAY100635, or [$^{18}$F]altanserin. The PET data were reconstructed using a Hanning filter (Nyquist cut-off) and corrected for decay, photon attenuation, and scatter.

An MRI scan was obtained for each baboon using a 1.5T GE Signa scanner (GE Medical Systems, Milwaukee, Wis.) equipped with a standard head coil. A volumetric spoiled gradient recalled (SPGR) MR sequence with parameters for high contrast among gray matter, white matter, and cerebral spinal fluid (CSF) was acquired in the coronal plane (TE=5, TR=24, flip angle=40°, slice thickness=1.5 mm, NEX=2, field of view 12 cm, voxel size=0.94×1.25×1.5 mm). Each individual baboon's MR image was coregistered to the PET data using the automated image registration (AIR) algorithm for cross-modality image alignment and reslicing. The initial 16 frames (0-9 minutes post-injection) of the dynamic PET images were summed together into images consisting of a single frame. Prior to co-registration, both the MR and summed PET images were edited using the ANALYZE software package (Mayo Clinic, Rochester, Minn.) to remove extracerebral tissues that could possibly confound the co-registration process. The edited MR images were then coregistered to the summed PET image and resliced to yield MR images in the same spatial orientation and resolution as the summed PET images. The co-registration of MR and PET datasets in the baboon has been demonstrated to be a reliable and robust application of the AIR method.

Regions of interest (ROIs) were defined on the coregistered MR image and applied to the dynamic PET datasets to determine regional time-activity data for white matter (cerebral white matter posterior to prefrontal cortex and anterior to lateral ventricles), temporal cortex, cerebellum (cerebellar cortex), and other brain areas (data not shown). The PET time-activity data were converted to units of microcuries per milliliter using a phantom-based calibration factor and were subsequently normalized to the injected dose and body mass of the animal ((% ID-kg)/g).

FIG. 1 shows a representative PET time-activity curve (TAC) of radioactivity in three brain regions of a baboon following the intravenous injection of Compound B. The TACs indicate excellent brain penetration of radioactivity at early time points (about 0.40% ID-kg/g, in reasonable agreement to the brain penetration of Compound B in mice at 2 minutes post-injection) in all three regions and relatively rapid clearance of the regional radioactivity from 0-90 minutes post-injection in the brain of this control baboon. Regions of brain containing higher levels of white matter demonstrated somewhat higher (~30%) concentrations of radioactivity at 90 minutes than regions that were dominated by gray matter such as temporal cortex. The concentration of radioactivity in baboon cortex was nearly identical to that in the cerebellar cortex at all time points. The rate of clearance of radioactivity was considerably slower from baboon brain than from mouse brain, with Compound B exhibiting a clearance half-time of about 17 minutes from baboon brain gray matter. The radiotracer Compound B exhibited an early-to-late brain radioactivity concentration in baboon brain of about 4 indicating that only about 25% of the peak maximum radioactivity remained in brain at later time points. These results were consistent with the expected absence of amyloid plaques in the brains of these control animals and indicated that very little radioactivity was retained in normal baboon brain. Comparison of the in vivo behavior of Compound B in baboon brain to that of the entry and clearance of other successful PET radioligands in a reference brain region devoid of specific binding sites (i.e., cerebellum) was useful.

Figure 2:
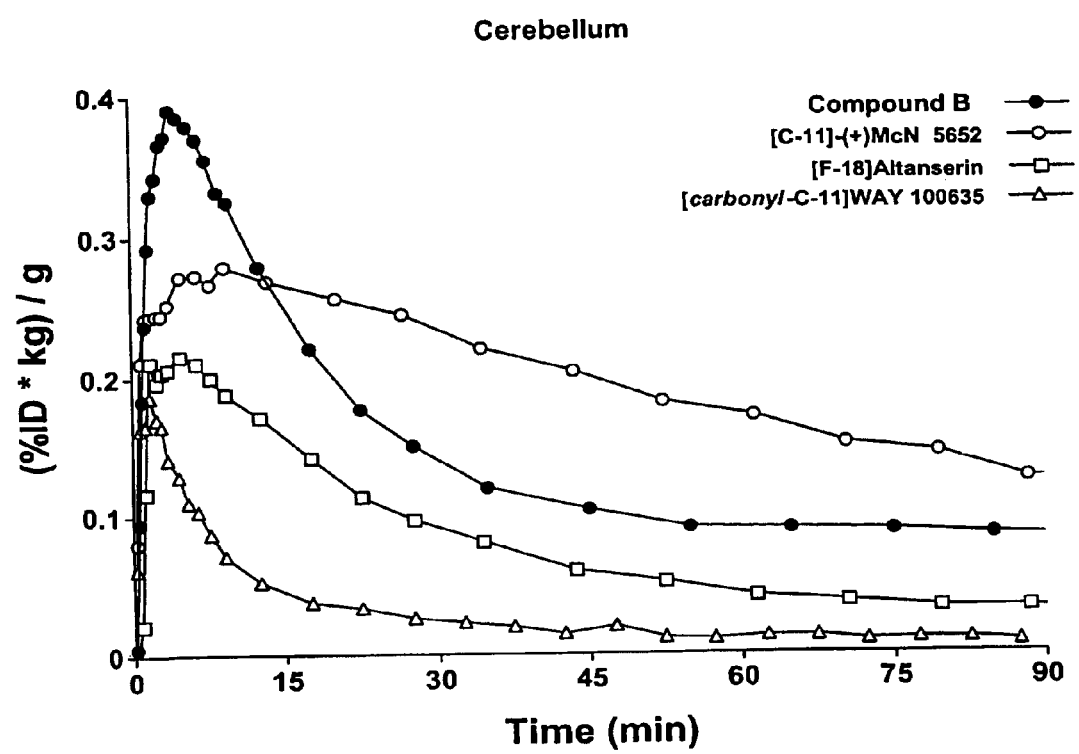
FIG. 2 shows time-activity curves of the penetration and clearance of radioactivity from baboon cerebellum (reference region devoid of specific binding) following the injection of the radioligands [carbonyl-$^{11}$C]WAY100635, [$^{11}$C](+)-McN5652, and [$^{18}$F]altanserin compared to the behavior of Compound B.

FIG. 2 compares the cerebellar TACs in baboons of [carbonyl-$^{11}$C]WAY100635, [$^{11}$C](+)-McN5652, [$^{18}$F]altanserin and Compound B. The relatively rapid non-specific binding clearance rates of [carbonyl-$^{11}$C]WAY100635 and [$^{18}$F]altanserin are important to the success of these PET radioligands for imaging the serotonin 5-HT$_{1A}$ and serotonin 5-HT$_{2A}$ receptor systems. In contrast, the relatively slow in vivo clearance of [$^{11}$C](+)-McN5652 has limited the usefulness of this radioligand for imaging the serotonin transporter system. The brain clearance properties of Compound B indicated that the relatively rapid rate of non-specific clearance of this radiotracer ($t_{1/2}$=17 minutes) was similar to that of other useful PET neuroreceptor imaging agents.

Figure 3:
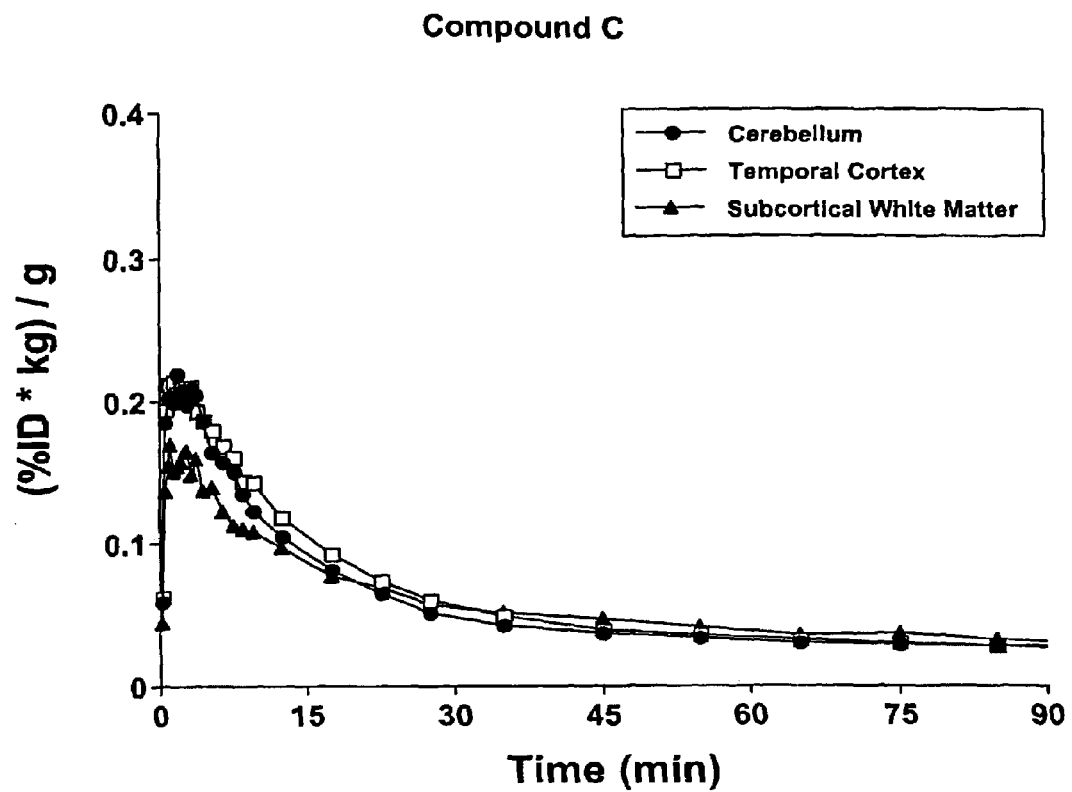
FIG. 3 shows time-activity curves of the penetration and clearance of radioactivity from three regions of baboon brain following the injection of Compound C (2-[4-(3-$^{18}$F-fluoropropylamino)-phenyl]benzothiazol-6-ol).

FIG. 3 shows a representative PET TAC of radioactivity in three brain regions of a baboon following the intravenous injection of Compound C. The TACs indicate excellent brain penetration of radioactivity at early time points (about 0.22% ID-kg/g, in good agreement to the brain penetration of Compound C in mice at 2 minutes post-injection) in all three regions and relatively rapid clearance of the regional radioactivity from 0-90 minutes post-injection in the brain of this control baboon. Regions of brain containing higher levels of white matter demonstrated slightly higher (<10%) concentrations of radioactivity at 90 minutes than regions that were dominated by gray matter such as temporal cortex. The concentration of radioactivity in baboon cortex was nearly identical to that in the cerebellar cortex at all time points. The rate of clearance of radioactivity was considerably slower from baboon brain than from mouse brain, with Compound C exhibiting a clearance half-time of about 10 minutes from baboon brain gray matter. The radiotracer Compound C exhibited an early-to-late brain radioactivity concentration in baboon brain of about 6 indicating that only about 15% of the peak maximum radioactivity remained in brain at later time points. These results were consistent with the expected absence of amyloid plaques in the brains of these control animals and indicated that very little radioactivity was retained in normal baboon brain. Comparison of the in vivo behavior of Compound C in baboon brain to that of the entry and clearance of other successful PET radioligands in a reference brain region devoid of specific binding sites (i.e., cerebellum) was useful.

Figure 4:
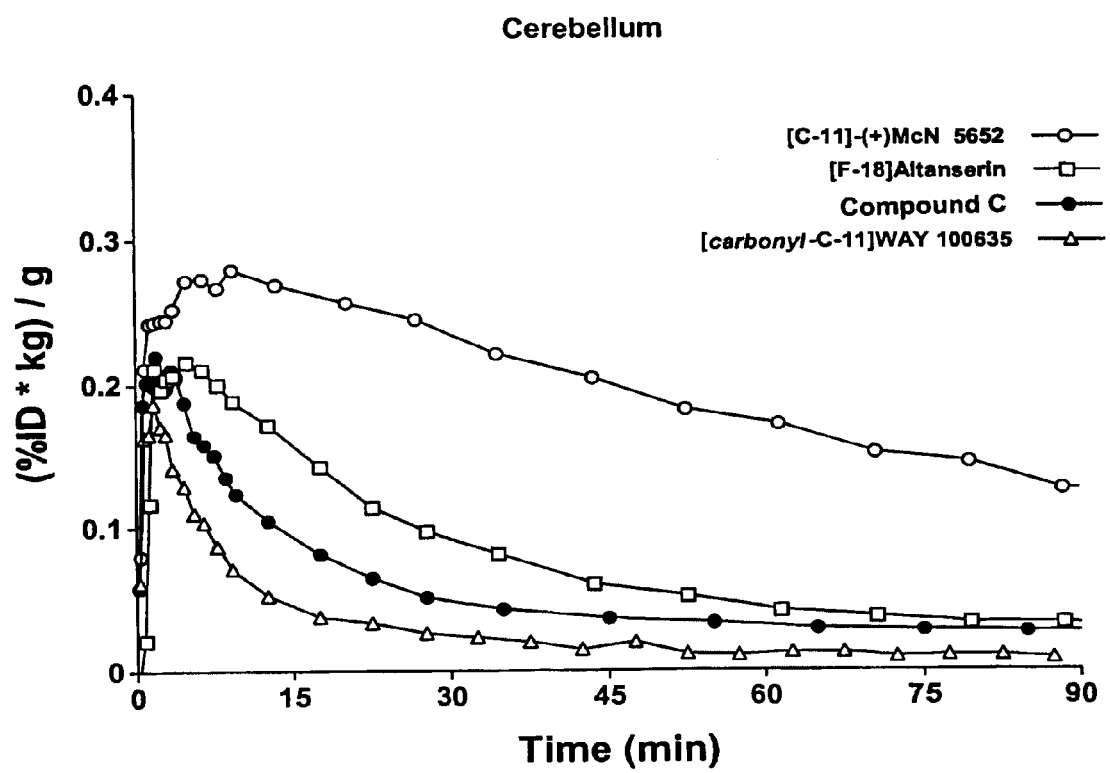
FIG. 4 shows time-activity curves of the penetration and clearance of radioactivity from baboon cerebellum (reference region devoid of specific binding) following the injection of the radioligands [carbonyl-$^{11}$C]WAY100635, [$^{11}$C](+)-McN5652, and [$^{18}$F]altanserin compared to the behavior of Compound C.

FIG. 4 compares the cerebellar TACs in baboons of [carbonyl-$^{11}$C]WAY100635, [$^{11}$C](+)-McN5652, [$^{18}$F]altanserin and Compound C. The relatively rapid non-specific binding clearance rates of [carbonyl-$^{11}$C]WAY100635 and [$^{18}$F]altanserin are important to the success of these PET radioligands for imaging the serotonin 5-HT$_{1A}$ and serotonin 5-HT$_{2A}$ receptor systems. In contrast, the relatively slow in vivo clearance of [$^{11}$C](+)-McN5652 has limited the usefulness of this radioligand for imaging the serotonin transporter system. The brain clearance properties of Compound C indicated that the relatively rapid rate of non-specific clearance of this radiotracer ($t_{1/2}$=10 minutes) was similar to that of other useful PET neuroreceptor imaging agents.

All publications, patents and patent applications identified above are herein incorporated by reference.

The invention being thus described, it will be apparent to those skilled in the art that the same may be varied in many ways without departing from the spirit and scope of the invention. Such variations are included within the scope of the invention to be claimed.

We claim:

1. A compound of formula I

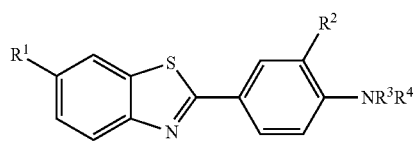

or a pharmaceutically acceptable salt, hydrate, solvate or prodrug of the compound, wherein:

R$^1$ is hydrogen, —OH, —NO$_2$, —CN, —COOR, —OCH$_2$OR, C$_1$-C$_6$ alkyl, C$_2$-C$_6$ alkenyl, C$_2$-C$_6$ alkynyl, C$_1$-C$_6$ alkoxy or halo;

R is C$_1$-C$_6$ alkyl;

R$^2$ is a radiofluoro;

R$^3$ is hydrogen, C$_1$-C$_6$ alkyl, C$_2$-C$_6$ alkenyl or C$_2$-C$_6$ alkynyl; and R$^4$ is hydrogen, C$_1$-C$_6$ alkyl, C$_2$-C$_6$ alkenyl or C$_2$-C$_6$ alkynyl.

2. The compound of claim 1, wherein:

R$^1$ is —OH or C$_1$-C$_6$ alkoxy;

R$^2$ is $^{18}$F;

R$^3$ and R$^4$ are independently selected from hydrogen and C$_1$-C$_6$ alkyl.

3. The compound of claim 1 having the following structure:

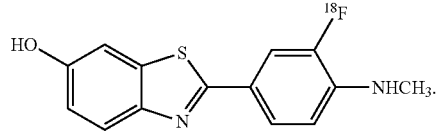

4. A pharmaceutical composition comprising
(i) an effective amount of a compound of claim 1; and
(ii) a pharmaceutically acceptable carrier.

* * * * *